(12) United States Patent
Lin et al.

(10) Patent No.: US 7,179,628 B2
(45) Date of Patent: Feb. 20, 2007

(54) TRANSGLUTAMINASE

(75) Inventors: Yi-Shin Lin, Hsinchu (TW); Mei-Li Chao, Hsinchu (TW); Chang-Hsiesh Liu, Shetou Township, Changhua County (TW); Min Tseng, Sinpu Township, Hsinchu County (TW); Shie-Jea Lin, Hsinchu (TW); Wen-Shen Chu, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 221 days.

(21) Appl. No.: 10/945,705

(22) Filed: Sep. 21, 2004

(65) Prior Publication Data
US 2005/0064571 A1   Mar. 24, 2005

(30) Foreign Application Priority Data
Sep. 22, 2003  (TW) .............................. 92126049 A

(51) Int. Cl.
  C12N 9/10   (2006.01)
  C12N 15/00  (2006.01)
  C12N 1/20   (2006.01)
  C07H 21/04  (2006.01)

(52) U.S. Cl. ................ 435/193; 435/320.1; 435/253.4; 435/252.3; 435/325; 435/252.35; 536/23.21

(58) Field of Classification Search ................ 435/193, 435/320.1, 253.4; 536/23.2
See application file for complete search history.

(56) References Cited

U.S. PATENT DOCUMENTS 5,420,025 A   5/1995   Takagi et al.
6,100,053 A   8/2000   Bech et al.

Primary Examiner—Rebecca E. Prouty
Assistant Examiner—Malgorzata A. Walicka
(74) Attorney, Agent, or Firm—Thomas, Kayden, Horstemeyer & Risley

(57) ABSTRACT

A DNA molecule encoding transglutaminase, a transglutaminase, an expression vector containing the DNA molecule, and a cell containing the expression vector.

6 Claims, 8 Drawing Sheets

```
  1 GATCCGGTAG GTGGGCGACG GTGAGATCTC AGAGCATGGA GCGCGTGAGT
 51 GCGATGTCGG CGCGCACCTG CCACGCCGCT TGATGCGCAC GGGCCAGGTG
101 AGGCTCGTCT GTCGCACGGC TCGCAGGCTG GCGGCGCAGT GCATCAGACG
151 AGGGGTGCAA GGACCGCATC TCCGCCGTTC TCGCTGACCC GGGCCGGCGC
201 GCGGCACTGC GCGACGGATG ACCCCAACG AGCGAAGGGT CCGCCGGTAG
251 CGAGTGGCGA AGTTCTTCCA GTACTTCAGG TGCGATGACC CTTCCGACTG
301 CGGTCCCGCA GCGAGTTGAC GGAGCTCCCA CAGTCGGTTC ACCCGGCTGA
351 ATGGGGCTCT TCGTCCCGGG CGGCGACGAC GCTTCAACC GCACCGTGGG
401 ATTCTCGACA ACATCGGTGC CGGCGTCGCT GCGAACCGCA CGCCACGAGC
451 AGGGAAACGC CGGCGCATCG CCTCCCCACG GGCCCGGCTCC CGCCACGAGC
501 GATACGGCCT GCGTGAGAGA TTGGCCGACT TTGAAACGC GTTGTTGCCG
551 GGGGGCCGGC GCGGGGACAT GATCACTGCT CGTATCAACC TGATCACTCA
601 TCCGGGAGCC GATACGTGAT ACGCCCACC GCTTTCCGTG CTCTTCCTGC
651 CGTCGCTGTC ACCCGGCCC CGCCCTGCTC CTCGCCCAGG GCGTGCAGGC
701 GGCTGGCCCG ACGCCCGTCG CCCGCGGGC CGCGCCGTGT CCCGCGCGTC
751 GCCAGGTCCG TCTGGTCGGC GCCGACTTCA TGCTCCCCG GCCGTCGTCC
801 GGGTCCGCT ACGGCGACCC CGGCCCCTTCG GAGCGGGCCG GCGTCGTCCC
851 TTCGGCGGCG ACGCTGATGT AGCGAGGCAC CGGTGCCGCC CGTGCCCGCC
901 GTGCCGGGCG GTCCGCCGGC CGCCAGGTCA TGGCCGGCGA CCGCACCGCC
951 ACCGCCATCT CCCGCCTTTG CCGCATCTCC TTCCGCCTCG TGGCGGCGTT
```

FIG. 2A

```
1001  CCATTCTGTC  GCCGCCACCG  CGCTCAGGAC  AGCGCGGCTG  CTTACCGCGA
1051  ACCCCTCATG  TGTCGTTCGC  TCGCATGCCC  GTTTCACGGG  AATCCACAAC
1101  AAGGAGTTA   CTGATTTCAT  GTACAAACGC  CGGAGTTTAC  TCGCGTTCGC
                              M   Y  K  R   R  S  L  L   A  F  A
1151             CACTGTGGGT  GCGCTGATAT  AGTCATGCCC  TCGGTCAGCC
                  T  V  G    A  L  I  C    V  M  P    S  V  S
1201  ATGCCGCCAG  CGGCGGCGAC  GGGGAATGGG  AGGGGTCCTA  CGCCGAAACG
       H  A  A  S   G  G  D   G  E  W    E  G  S  Y   A  E  T
1251  CACGACCTGA  CGGCGGGAGGA  CGGGGTCAAC  ATCAACGCGC  TGAACAAAAG
       H  D  L    T  A  E  D    G  Q       I  N  A    L  N  K  R
1301  AGCTCTGACT  GCTCTTCCGG  CGTCAAGAAC  GCCGGCGGAA  TTGTCGCCGA
       A  L  T    L  F  R     V  K  N    P  G  N  S    L  S  P
1351  GCGCCAGTGC  AGCCGCTCAA  CCCCCCGACG  GCCGTCGATGA  CAGGGTGACC
       S  A  S  A   Q          P           A  V  D  D    R  V  T
1401  CCTCCCGCCG  ACTACGGTCG  CCGGATGCCT  GACGCCGTACC  GGGCCTACGG
       P  P  A    E  P  L  N   R  M  P    D  A  Y     R  A  Y  G
1451  AGGCAGGGCC  ACTACGGTCG  TCAACAACTA  CATACCGCAAG  TGGCAGCAGG
       G  R  A    T  T  V    V  N  N  Y   I  R  K    W  Q  Q
1501  TCTACAGTCA  ACGCGGGGGC  AACCCACAGC  AAATGACCGA  AGAGCAGCGA
       V  Y  S  Q   R  G  G    N  P  Q     Q  M  T  E    E  Q  R
```

FIG. 2B

```
1551  GAACAACTGT  CCTACGGCTG  CGTCGGCGTC  ACCTGGGTCA  ATACAGGCCC
       E  Q  L    S  Y  G  C    V  G  V    T  W  V    N  T  G  P

1601  CTACCCGACG  AACAAACTCG  CGTTCGCGTT  CTTCGACGAG  AACAAGTACA
       Y  P  T    N  K  L    A  F  A  F    F  D  E    N  K  Y

1651  AGAACGACCT  GGAAAACAGC  AGACCGCGAA  CCAACGCGAC  GCAGGCGGAG
       K  N  D  L    E  N  S    R  P  R    P  N  E  T    Q  A  E

1701  TTCGAGGGGC  GCATCGCCAA  GGACAGTTTC  GATGAGGGAA  AGGGTTTCAA
       F  E  G  R    I  A  K    D  S  F    D  E  G    K  G  F  K

1751  GCGGGGCGCGT  GAGGTGGCAT  CCGTCATGAA  CAAGGCCCTG  GATAACGCGC
       R  A  R    E  V  A    S  V  M  N    K  A  L    D  N  A

1801  ACGACGAGGA  GACTTACATC  GGCCACCTCA  AGACAGAGCT  CGCGAACAAA
       H  D  E  E    T  Y  I    G  H  L    K  T  E  L    A  N  K

1851  AACGACGCTC  TGCTCTACGA  GGACAGCCGC  TCGAGCTTTT  ACTCGGCGCT
       N  D  A  L    L  Y  E    D  S  R    S  S  F    Y  S  A  L

1901  GAGGAATACG  CCGTCCTTCA  AGGAAAGGGA  TGGAGGCAAC  TACGACCCGT
       R  N  T    P  S  F    K  E  R  D    G  G  N    Y  D  P

1951  CCAAGATGAA  GGCGGTGGTC  TACTCGAAGC  ACTTCTGGAG  CGGGCAGGAC
       S  K  M  K    A  V  V    Y  S  K    H  F  W  S    G  Q  D

2001  CAGCGGGGCT  CCTCCGAGAA  GAGGAAGTAC  GGTGACCCGG  ACGCCTTCCG
       Q  R  G  S    E  K    R  K  Y    G  D  P    D  A  F  R
```

FIG. 2C

```
2051  CCCCGGCCAG  GGCACAGGTC  TGGTAGACAT  GTCGAGGGAC  AGGAACATTC
       P  G  Q     G  T  G     L  V  D  M   S  R  D    R  N  I
2101  CGCGTAGTCC  CGCAAAACCT  GGCGAAAGTT  GGGTCAATTT  CGACTACGGC
       P  R  S    P  A  K  P   A  E  S  F  G  S  I    R  L  R
2151  TGGTTCGGGG  CTCAGGCAGA  AGCGGGATGC  GACAAAACCG  TATGGACCCA
       W  F  G    A  Q  A  E   A  D  A    D  K  T     V  W  T  H
2201  CGCCAACCAC  TATCATGCGC  CCAATGGGCGG  CATGGGCCCC  ATGAACGTAT
       A  N  H    Y  H  A     P  N  G  G   M  G  P    M  N  V
2251  ACGAGAGCAA  GTTCCGGAAC  TGGTCTGCGG  GGTACGGCGGA  CTTCGACCGC
       Y  E  S  K  F  R  N    W  S  A     G  Y  A  D   F  D  R
2301  GGAGCCTACG  TCATCACGTT  CATACCCAAG  AGCTGGAACA  CCGCCCCCGC
       G  A  Y    V  I  T  F   I  P  K    S  W  N     T  A  P  A
2351  CGAGGTGAAG  CAGGGCTGGC  CGTAACAGAG  CCGGGCACGA  GGGCCGGGCC
       E  V  K    Q  G  W     P  *
2401  ACCCGGCCCT  CTCCGCCCGG  CCGCCACACG  CCGGCAGTCA  TCCCGGATGT
2451  GTTACGGAGC  GCCGGAGGTG  CGCTCGCCCC  AGCGCTTCGG  GGAACTGGCG
2501  GCACCTGGGC  AGCGCAGCGC  GGAGAGAAGT  GAAGGGCACG  AGCCGGGCGG
2551  CGCATGCCCT  TCAGCCATCC  GCGGGGAGCT  GATGGATGCG  CAGTTCAACG
2601  AACAACCGGC  TACGGCGGTC  ACGCCCGTGC  CGTGGGGGTG  GTGCTGCTGG
```

FIG. 2D

```
2651  GGCTCAGGTG  CGTTGTGGCC  CTGTGCTCGT  CGACTGCCCC  TGGAACGGGG
2701  GCGGGCACAG  GGCCACCGGC  CTGTCAGGGC  AGGCCGTGAC  GACGGGCGCA
2751  GCACGCACCC  ACCCGTCGTG  ATCTCCAGCC  TGCTGCGCTG  GGAGCGCGGG
2801  TGCCTCGCCC  ACCTCGGAGG  CGGGCGAGGC  AATTACGTAC  ACCTCGGTGT
2851  TCATCGGCCC  TCTGTCCGGG  AACCCGTGAT  GAACTAGCCG  GAGCCGTTGG
2901  CTGCCGGATC
```

FIG. 2E

TRANSGLUTAMINASE

CROSS-REFERENCE TO RELATED APPLICATION

This application claims benefit of and priority to Taiwanese Patent Application No. 92126049 filed on Sep. 22, 2003, and which is incorporated by reference in its entirety.

BACKGROUND

The invention relates to a transglutaminase gene and a transglutaminase obtained therefrom.

Transglutaminase (hereafter, referred to as TGase) catalyzes intramolecular or intermolecular formation of $\epsilon$-($\gamma$-Gln)-Lys covalent bond, and the crosslink between protein molecules forms gel protein with a tertiary structure. The gel protein can be applied in the food-processing industry, including meat, fish, soybean, wheat, milk, or egg, as a new protein food or gel membrane.

TGases has been found in various tissues and organs of mammals and plants. The first commercialized TGase was isolated from the liver of guinea pig, however, its price is relatively high, about 80 US dollars per unit, because of the difficulties of acquisition. The high price also restricts its use in the food-processing industry. In addition, the technology of isolating TGases from fish or plants is immature. Large scale production of TGase is, therefore, an important task.

It has been found that many strains of microbes produce TGases. Those whose TGases have been cloned include *Streptoverticillium* S-8112 (Washizu et al., 1994), *Streptoverticillium mobaraense* (Pasternack et al., 1998), *Streptomyces lydicus* (Bech et al., 1996), *Bacillus subtilis* (Kobayashi et al., 1998). Those having exocrine TGase include S-8112 (Ando et al., 1989), *S. mobaraense* (Pasternack et al.,, 1998), *S. cinnamoneum* (Duran et al., 1998), and *S. lydicus* (Bech et al., 1996). According to Wu et al. (1996), most TGases derived from *Streptoverticillium* sp. are exocrine. In the twenty strains of *Streptoverticillium* sp. tested by Wu et al., TGase derived from *Streptoverticillium ladakanum* has highest activity. The expression activity of those genes, however, are still restricted in some way, therefore, obtaining a TGase with high expression activity is still required.

SUMMARY

The inventors screened out a TGase producing strain, *S. platensis,* from more than 300 strains of *Streptomyces* stored in the Bioresources Collection and Research Center of the Food Industry Research and Development Institute. Overexpression of the cloned TGase gene from *S. platensis* produce a TGase with activity of 5.7 U/ml, which is 5.7 times that of the wild type. The invention was then achieved.

Accordingly, an embodiment of the invention provides a DNA molecule isolated from *Streptomyces platensis* encoding TGase, and the DNA molecule is composed of a nucleotide sequence of SEQ ID NO: 1.

In the DNA molecule derived from *S. platensis,* the sequence encoding TGase is composed of a nucleotide sequence of SEQ ID NO: 3.

Also provided is a TGase composed of an amino acid sequence of SEQ ID NO: 2.

Another embodiment of the invention provides an expression vector of TGase including a DNA sequence encoding TGase, composed of a nucleotide sequence of SEQ ID NO: 1.

Yet another embodiment of the invention provides a host cell including the expression vector of TGase. In this embodiment of the invention, the host cell is *Streptomzyces lividans*.

BRIEF DESCRIPTION OF THE DRAWINGS

Embodiments of the invention can be more fully understood and further advantages become apparent when reference is made to the following description and the accompanying drawings in which:

FIG. 2A–2E illustrate the nucleotide and amino acid sequences of the *S. platensis* TGase gene in an embodiment of the invention. The frame region is the predictive ribosomal binding site, the underlined region is the mature form of the enzyme, and the bold words represent the amino acid sequence of the enzymatic active center, YGCV.

DETAILED DESCRIPTION

Figure 1:
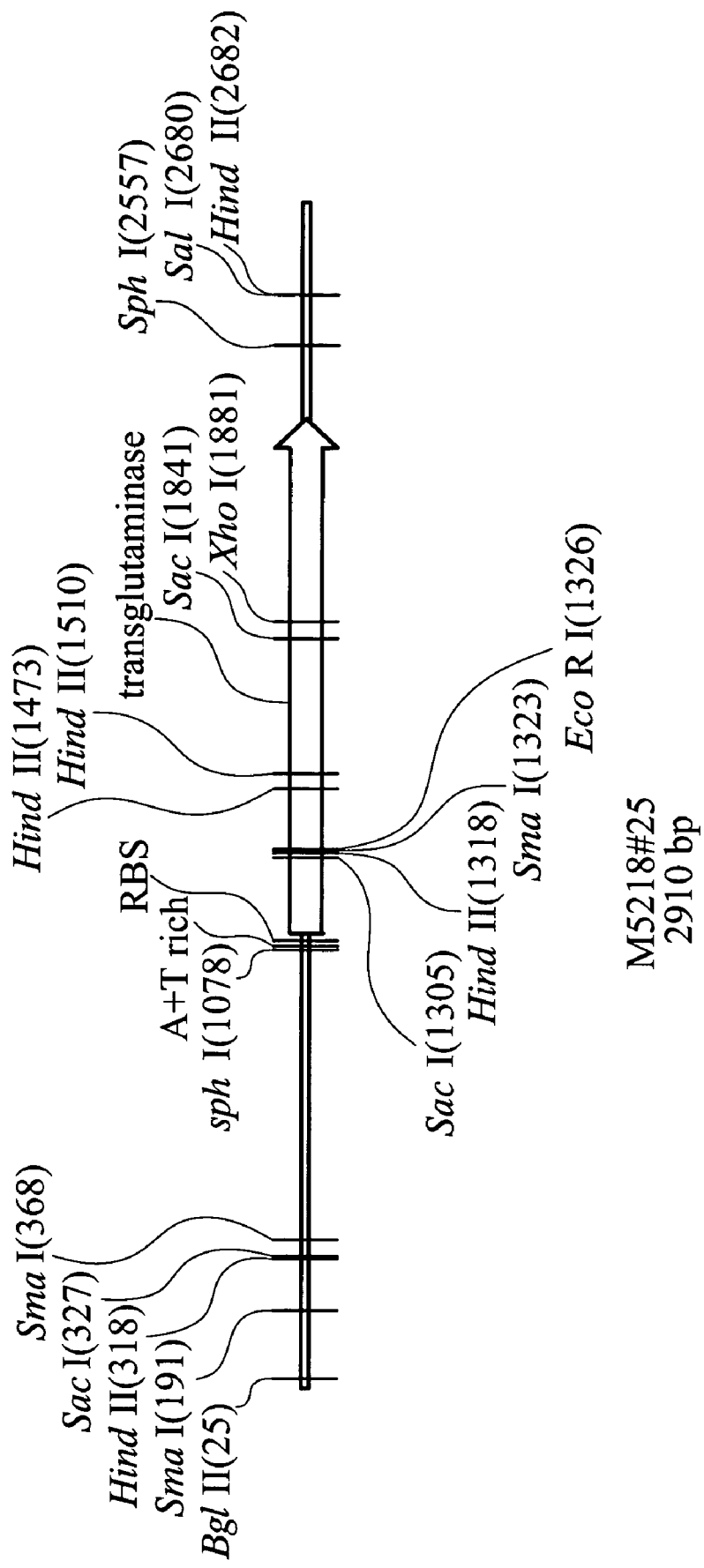
FIG. 1 illustrates the restriction map of the entire *S. platensis* TGase gene sequence of 2.9 Kb in an embodiment of the invention.

More than 300 strains of *Streptomyces* stored in the Bioresource collection and research center of the Food Industry Research and Development Institute were screened and a strain M5218 was found having high activity of TGase, about 1.0 U/ml. After morphological, physiological, biochemical characteristic analysis and 16s rRNA sequence comparison, the strain was identified as *Streptomyces platensis*. The chromosomal DNA of the strain was digested with restriction enzyme Sau3AI, DNA fragments of 3–5 kb were then separated by electrophoresis and isolated from the gel. These DNA fragments were ligated with pIJ702 which is a high-copy vector and the plasmids were transformed into host *S. lividans* JT46 for overexpression. The cloned, sequenced, and analyzed TGase gene has a length of 1.25 kb and can be translated to be 418 amino acids. The transformed clone denominated as 25-2 was incubated in a 250 mL Erlenmeyer flask with 50 mL of media under 250 rpm vibration at 30° C. for 2 days. The TGase activity can be 5.7 U/mL, 5.7 times that of wild type.

Practical examples are described herein.

EXAMPLES

Above all, the sources of the materials used in the examples are illustrated herein. Restriction enzymes and T4 DNA ligase were purchased from Boehringer Mannheim and New England Biolab and the protocol is according to the instruction therewith. AmpliTaq Gold™ DNA polymerase was purchase from PE Applied Biosystems, Geneclean III from Bio101, thiostrepton from Sigma, and agarose from Gibco BRL. In addition, the carbon source of the medium includes 1% glucose, 1% glycerol, 1% starch, 0.1% sucrose, 1% fructose; the nitrogen source and salts include 0.5% glycine, 0.05% casein, 0.5% yeast extract, 0.05% terptone peptone, 0.05% $(NH_4)_2SO_4$, 0.05% polypeptone, 0.2% $MgSO_4 \cdot 7H_2O$, 0.2% $K_2HPO_4$.

Example 1

Cloning of TGase Gene with High Productivity 300 strains of *Streptomyces* stored in the Bioresource collection and research center of the Food Industry Research and Development Institute were recovered and cultured by loop streak method in ISP3 medium at 30° C. for 3–4 days. Single colonies were selected and TGase producing clones were screened by qualitative analysis.

The qualitative analysis is as follows. The enzyme substrates including 1M Tris-HCl, pH6.0, 40 µl, 0.15M CBZ-Q-G, pH6.0, 20 µl, and 4M hydroxylamine, pH6.0, 20 µl were added in each well of a 96-well microplaate. The colonies were seeded to each well and incubated at 37° C. for 8 to 16 hours. Eighty µl of developing agent containing 15% TCA, 5% $FeCl_3$ in 2.5N HCl and 5% $FeCl_3$ in 0.1N HCl of volume ratio 1:1:1 was added to terminate the reaction. TGase activity was determined by the naked eye, and red-brown color represents TGase activity.

Five clones: M5218, M5802, M6701, PT7-1, and HTII11-2, were found having TGase activity, and M5218 has the hightest TGase activity of 1.0 U/mL. After morphological, physiological, biochemical characteristic analysis and 16s rRNA sequence comparison, the strain was identified as *Streptomyces platensis*.

Example 2

Cloning of TGase gene from Streptomycese platensis

The isolation of chromosomal DNA of *Streptomyces platensis* and plasmid DNA, and preparation and transformation of protoplast are according to Hopwood et al. (1985). Chromosomal DNA of *S. platensis* was digested by Sau3AI and separated by electrophoresis. DNA fragments with a size of 3–5 kb were purified and ligated into pIJ702 (obtained from the Bioresource collection and research center of the Food Industry Research and Development Institute) with BglII site. The ligation reactant was transformed into host *Streptomyces lividans* JT46 (provided by Carton W.-S. Chen). The transformants were screened in R2YE plate by thiostrepton (purchased from Sigma chemical). The host *Streptomyces lividans* JT46 was chosen for the recombinant DNA since it does not have TGase activity. Hundreds of the transformants were cultured at 30° C. for 2 days and one transformant 25-2 was screened having TGase activity. The transformant 25-2 has been deposited in the Bioresource collection and research center of the Food Industry Research and Development Institute on Sep. 2, 2003 numbered as BCRC 940430 and in the American type culture collection on Sep. 29, 2003 numbered as PTA-5442. The recombinant plasmid containing TGase gene from *S. platensis* was restriction analyzed and hybridized with DNA. It was found that TGase gene is located in a 2.9 kb KpnI fragment as shown in FIG. 1. The fragment was cloned and ligated into pMTL23 (obtained from the Bioresource collection and research center of the Food Industry Research and Development Institute) with KpnI cutting site and the resulting plasmid was denominated as pAE023. DNA sequencing was performed to confirm the insertion. The DNA fragment was replicated under *E. coli* and the reaction is performed with Bigdye™terminator RR mix (PE Applied Biosystems) by autosequencer ABI PRISM™ Model 310. The nucleotide sequence is shown as FIG. 2A–2C. The whole KpnI fragment has 2910 nucleotides. Sequence analysis was performed by Wisconsin Sequence Analysis Package (version 8.0, Genetics Computing Group) to analyze codon preference and sequence similarity comparison. The GCG codon preference analysis predicts that one reading frame from nucleotides 1119 to 2375 has a gene, as shown in FIG. 2A–2E. The nucleotide sequence of the gene was analyzed by BLASTN as similar to TGase of *Streptoverticillium* S-8112. The predicted amino acid sequence is shown in FIG. 2A–2C and has 418 amino acids with a molecular weight of 46511.30 Daltons. The result was compared with the mature form of TGase from *S. ladaksnum* by Kanai. et al. (1993) and the predicted mature form of TGase. from *S. platensis* starts at nucleotide 88 and has 330 amino acids with a molecular weight of 37,468.21 Daltons and an isoelectric point of 7.17. Nucleotides −12~−15 from the starting amino acid of TGase from *S. platensis* are GGAG sequence, which is a ribosome binding site as shown in FIG. 2B, frame region. An AT-rich region was found at 5' untranslated region of the gene, nucleotides 1066–1117, as shown in FIG. 2B. This region is predicted as a promoter region, however, no sequence similar to CAAT box or TATA box of *E. coli* promoter was found with sequence comparison. Other researchers also found that the promoter regions of *Streptomyces* species are not consensus as that of *E. coli* (Gilber et al., 1995).

Example 3

Expression of TGase gene of S. platensis in S. lividans

Figure 3:
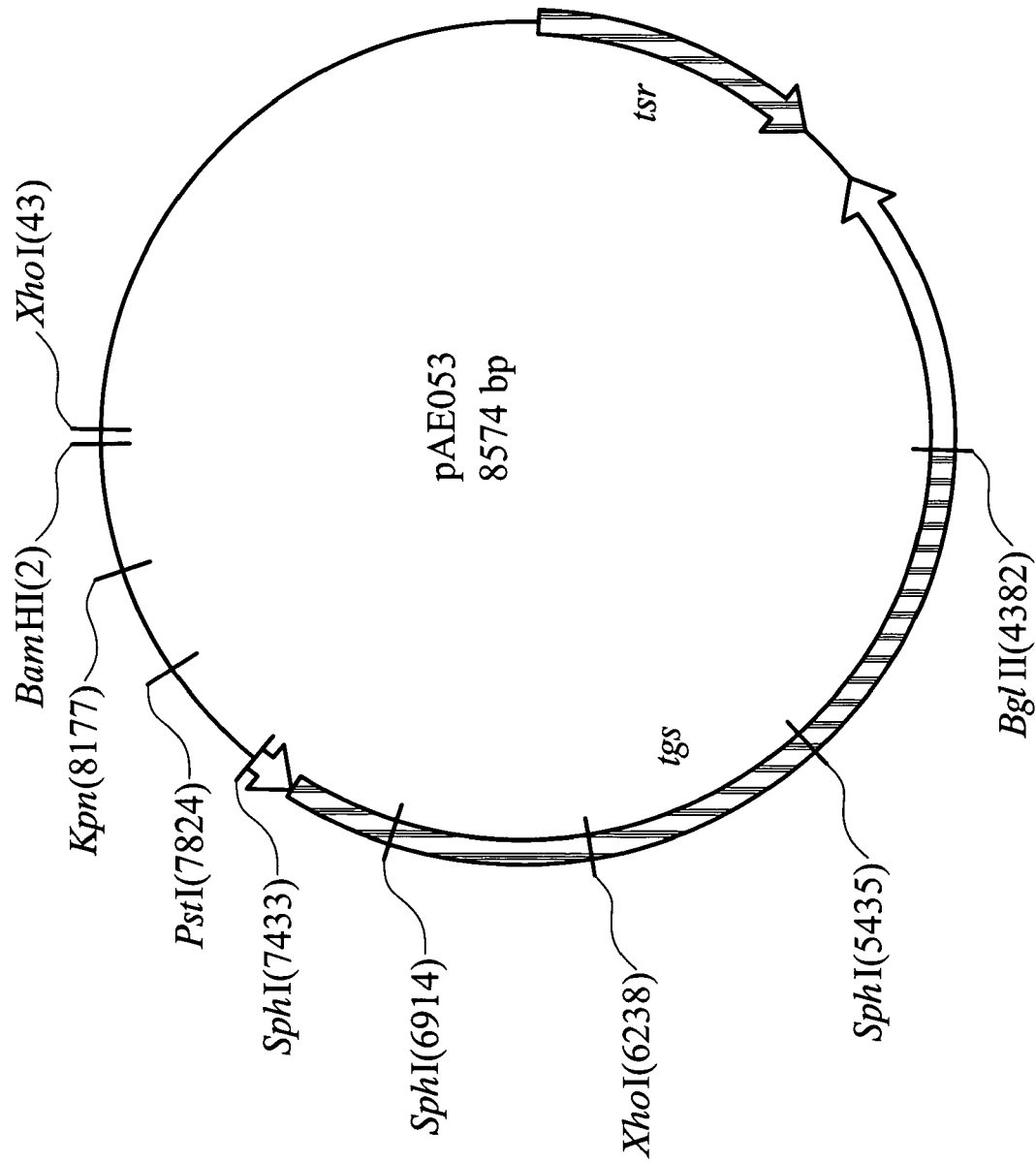
FIG. 3 illustrates the restriction map of pAE053. The abbreviation: tgs, TGase gene; tsr, thistrepton gene.

The standard recombinant DNA manipulation is performed according to Sambrook et al. (1989). pAE023 was digested with BglII and BamHI and 2.9 kb of DNA fragment containing TGase gene was purified and ligated to the BglII restriction site of pIJ702. The ligation product dominated as pAE053 (FIG. 3) was expressed in *S. lividans* JT46.

The TGase activity was determined by the following procedure: The spores of TGase-producing bacteria were inoculated in a 250 mL Erlenmeyer flask with 30 mL of media (carbon source: 1% glucose, 1% glycerol, 1% starch, 0.1% sucrose, 1% fructose; nitrogen source and salts: 0.5% glycine, 0.05% casein, 0.5% yeast extract, 0.05% tryptone peptone, 0.05% $(NH_4)_2SO_4$, 0.05% polypeptone, 0.2% $MgSO_4 \cdot 7H_2O$, 0.2% $K_2HPO_4$) with one duplicate under 220 rpm horizontal vibration at 30° C. The cultures were centrifuged under 6,000 g for 10 min and 50 µl of the supernatants were collected and mixed with 350 µl of 1M Tris-HCl (pH6.0), 80 µl of 0.15M CBZ-Gln-Gly (pH 6.0), and 20 µl of 4M hydroxylamine. After water incubation at 37° C. for 10 min, 500 µl of developer containing 1:1:1 of 15% TCA, 5% $FeCl_3$ in 2.5N HCl and 5% $FeCl_3$ in 0.1N HCl was immediately added. The absorbance of the mixture was measured by a spectrophotometer under 525 nm. Five hundred µl standard solution of L-glutamic acid-γ-monohydroxymic acid with different concentrations, 0 mM, 0.5 mM, 1.0 mM, and 2.0 mM were mixed with the developer separately and the absorbance of these standard solutions was measured by a spectrophotometer under 525 nm. A standard curve was obtained according to the standard solutions and the absorbance thereof, and the concentration of the product can be obtained with the measured absorbance and the standard curve. The TGase activity is defined as µmole amount of the reactant produced by the enzyme solution per min; the unit is µmmol/min.

Figure 4:
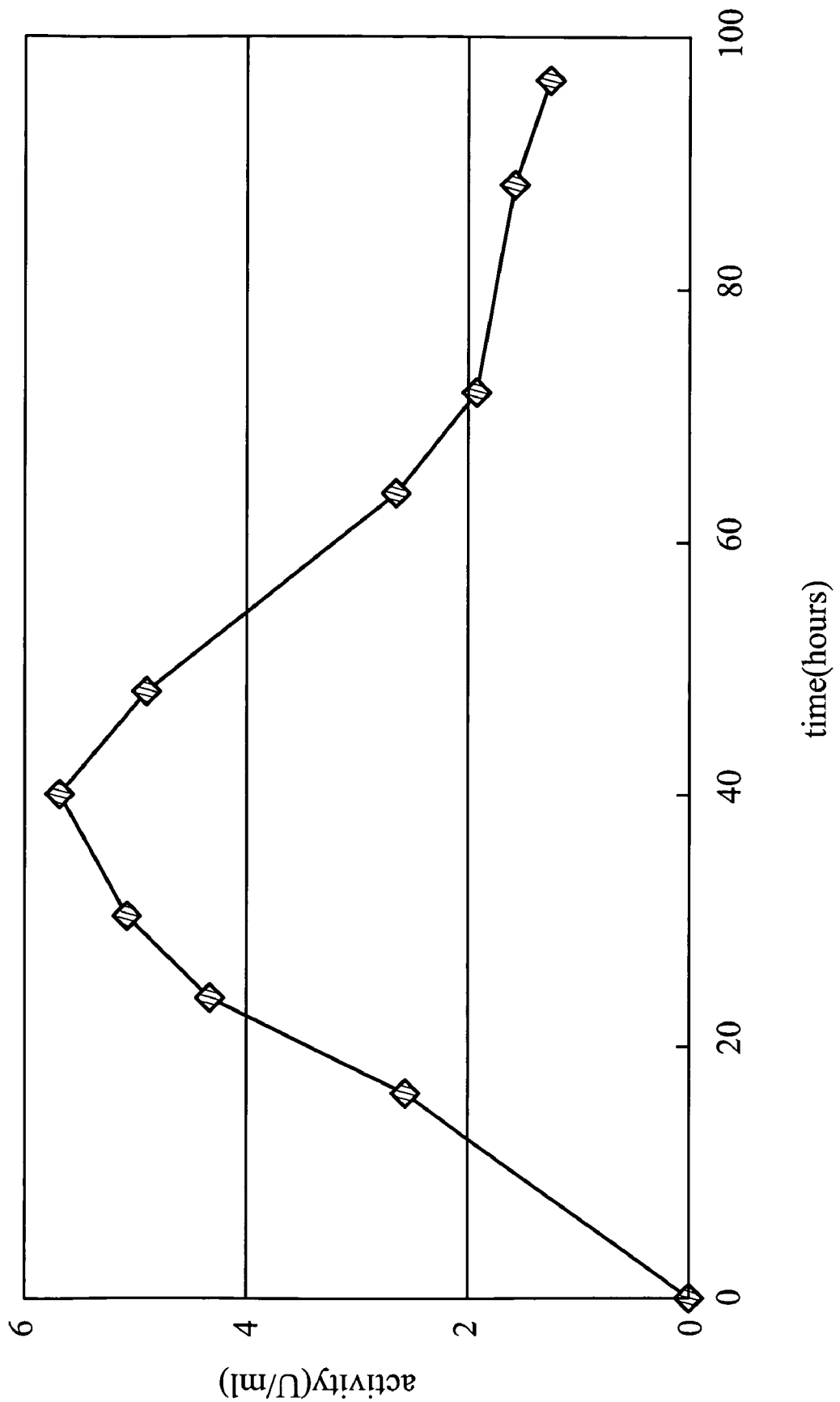
FIG. 4 illustrates the relation of TGase activity to culturing time in transformant 25-2.

The TGase activity in the supernatants was measured every 12 hours. The transformant 25-2 has the highest activity at 40 hours, up to 5.7 U/ml (FIG. 4). The molecular weight of TGase from *S. platensis* is determined as 40.4 kD by ammonium sulfate precipitation, ion exchange, and SDS electrophoresis (data not shown), which is larger than the predicted MW of 37.5 kD.

Example 4

TGase Seqeucne Comparison of an Embodiment of the Invention and the Known Sequence TGase seqeuence comparison of the gene derived from *S. platensis* and the published sequences shows that TGase of an embodiment of the invention has 78.55% similarity in amino acid sequence and 82.44% in nucleotide sequence to that derived from *Streptoverticillium mobaraense* DSMZ published by Pastermack et al. and 89.54% similarity in amino acid sequence and 82.44% in nucleotide sequence to that derived from *S. lydicus* published in U.S. Pat. No. 6,100,053 to Bech et al. Compared to the gene derived from *Streptoverticillium* species published in U.S. Pat. No. 5,420,025 to Takagi et al., it has 79.33% similarity in amino acid and 81.50% in nucleotide sequence. Only Bech et al. discloses that the gene has a determined activity of 2.4 U/ml. The activity detection of the preferred embodiment of the invention is by standard solution of L-glutamic acid-γ-monohydroxymic acid and developer, which is not more sensitive than radio-detection of Bech et al, however, the result of this embodiment of the invention (5.7 U/ml) is more than two times that of Bech et al. Therefore, it is obvious that the gene sequence of this embodiment of the invention is superior to any known sequences. The gene sequence of this embodiment of the invention can be used with suitable host cells for mass production of TGase with high activity. The cost of producing TGase can be greatly reduced.

While the invention has been described by way of example and in terms of preferred embodiment, it is to be understood that the invention is not limited thereto.

What is claimed is:

1. An isolated and purified nucleic acid comprising SEQ ID NO: 1, wherein the SEQ ID NO: 1 is derived from *Streptomyces platensis* and transglutaminase is encoded thereby.

2. An isolated and purified nucleic acid comprising SEQ ID NO: 3, wherein the SEQ ID NO: 3 is derived from *Streptomyces platensis* and transglutaminase is encoded thereby.

3. An isolated and purified protein, comprising an amino acid sequence of SEQ ID NO: 2.

4. An expression vector comprising SEQ ID NO: 1.

5. An isolated host cell that comprises expression vector of claim 4.

6. The cell of claim 5, wherein the cell is *Streptomyces lividans*.

* * * * *

SEQUENCE LISTING

<160> NUMBER OF SEQ ID NOS: 3

<210> SEQ ID NO 1
<211> LENGTH: 2910
<212> TYPE: DNA
<213> ORGANISM: Streptomyces platensis

<400> SEQUENCE: 1

```
gatccggtag gtgggcgacg gtgagatctc agagcatgga gcgcgtgagt gcgatgtcgg      60
cgcgcacctg ccacgccgct tgatgcgcac gggccaggtg aggctcgtct gtcgcacggc     120
tcgcaggctg gcggcgcagt gcatcagacg aggggtgcaa ggaccgcatc tccgccgttc     180
tcgctgaccc gggccggcgc gcggcactgc gcgacggatg accccaacg agcgaagggt      240 ccgccggtag cgagtgcga agttcttcca gtacttcagg tgcgatgacc cttccgactg      300
cggtcccgca gcgagttgac ggagctccca cagtcggttc acccggctga atggggctct      360
tcgtcccggg cggcgacgac ggcttcaacc gcaccgtggg attctcgaca acatcggtgc      420
cggcgtcgct gcgaaccgca cgccacgagc agggaaacgc cggcgcatcg cctccccacg      480
ggccggctcc tgcatggccg gatacggcct gcgtgagaga ttggccgact ttgaaaccgc      540
gttgttgccg gggggccggc gcggggacat gatcactgct cgtatcaacc tgatcactca      600
tccgggagcc gatacgtgat acgccccacc gctttccgtg ctcttcctgc cgtcgctgtc      660
accgcggccc cgccctgctc ctcgcccagg gcgtgcaggc ggctggcccg acgcccgtcg      720
ccccggcggc cgccgctgtc ggccgtcccg gccaggtccg tctggtcggc gccgacttca      780
tgcgctcccg cccgcgcgtc ggggtccgct acggcgaccc cggcccttcg gagcgggccg      840
gcgtcgtccc ttcggcggcg acgctgatgt agcgaggcac cggtgccgcc cgtgccgccc      900
gtgccgggcg gtccgccggc cgccaggtca tggccggcga ccgcaccgcc accgccatct      960
cccgcctttg ccgcatctcc ttccgcctcg tggcggcgtt ccattctgtc gccgccaccg     1020
cgctcaggac agcgcggctg cttaccgcga accctcatg tgtcgttcgc tcgcatgccc      1080
gtttcacggg aatccacaac aagggagtta ctgatttcat gtacaaacgc cggagtttac     1140
tcgcgttcgc cactgtgggt gcgctgatat gcaccgccgg agtcatgccg tcggtcagcc     1200
atgccgccag cggcggcgac ggggaatggg aggggtccta cgccgaaacg cacgacctga     1260
```

-continued

```
cggcggagga cgtcaagaac atcaacgcgc tgaacaaaag agctctgact gcgggtcaac    1320
ccgggaattc gccggcggaa ttgtcgccga gcgccagtgc gctcttccgg gcccccgacg    1380
ccgtcgatga cagggtgacc cctcccgccg agccgctcaa ccggatgcct gacgcgtacc    1440
gggcctacgg aggcagggcc actacggtcg tcaacaacta catacgcaag tggcagcagg    1500
tctacagtca acgcggcggc aacccacagc aaatgaccga agagcagcga gaacaactgt    1560
cctacggctg cgtcggcgtc acctgggtca atacaggccc ctacccgacg aacaaactcg    1620
cgttcgcgtt cttcgacgag aacaagtaca agaacgacct ggaaaacagc agaccgcgac    1680
ccaacgagac gcaggcggag ttcgaggggc gcatcgccaa ggacagtttc gatgagggaa    1740
agggtttcaa gcgggcgcgt gaggtggcat ccgtcatgaa caaggccctg gataacgcgc    1800
acgacgagga gacttacatc ggccacctca agacagagct cgcgaacaaa aacgacgctc    1860
tgctctacga ggacagccgc tcgagctttt actcggcgct gaggaatacg ccgtccttca    1920
aggaaaggga tggaggcaac tacgacccgt ccaagatgaa ggcggtggtc tactcgaagc    1980
acttctggag cgggcaggac cagcggggct cctccgagaa gaggaagtac ggtgacccgg    2040
acgccttccg ccccggccag ggcacaggtc tggtagacat gtcgagggac aggaacattc    2100
cgcgtagtcc cgcaaaacct ggcgaaagtt gggtcaattt cgactacggc tggttcgggg    2160
ctcaggcaga gcggatgcc gacaaaaccg tatggaccca cgccaaccac tatcatgcgc    2220
ccaatggcgg catgggcccc atgaacgtat acgagagcaa gttccggaac tggtctgcgg    2280
ggtacgcgga cttcgaccgc ggagcctacg tcatcacgtt catacccaag agctggaaca    2340
ccgcccccgc cgaggtgaag cagggctggc cgtaacagag ccgggcacga gggccgggcc    2400
acccggccct ctccgccggc cgccacacg ccggcagtca tcccggatgt gttacggagc    2460
gccggaggtg cgctcgcccc agcgcttcgg ggaactggcg gcacctgggc agcgcagcgc    2520
ggagagaagt gaagggcacg agccgggcgg cgcatgccct tcagccatcc gcggggagct    2580
gatggatgcg cagttcaacg aacaaccggc tacggcggtc acgcccgtgc cgtggcggtg    2640
gtgctgctgg ggctcaggtg cgttgtggcc ctgtgctcgt cgactgcccc tggaacgggg    2700
gcgggcacag ggccaccggc ctgtcagggc aggccgtgac gacgggcgca gcacgcaccc    2760
acccgtcgtg atctccagcc tgctgcgctg ggagcgcggg tgcctcgccc acctcggagg    2820
cgggcgaggc aattacgtac acctcggtgt tcatcggccc tctgtccggg aacccgtgat    2880
gaactagccg gagccgttgg ctgccggatc                                     2910
```

<210> SEQ ID NO 2
<211> LENGTH: 418
<212> TYPE: PRT
<213> ORGANISM: Streptomyces platensis

<400> SEQUENCE: 2

```
Met Tyr Lys Arg Arg Ser Leu Leu Ala Phe Ala Thr Val Gly Ala Leu
1               5                   10                  15

Ile Cys Thr Ala Gly Val Met Pro Ser Val Ser His Ala Ala Ser Gly
            20                  25                  30

Gly Asp Gly Glu Trp Glu Gly Ser Tyr Ala Glu Thr His Asp Leu Thr
        35                  40                  45

Ala Glu Asp Val Lys Asn Ile Asn Ala Leu Asn Lys Arg Ala Leu Thr
    50                  55                  60

Ala Gly Gln Pro Gly Asn Ser Pro Ala Glu Leu Ser Pro Ser Ala Ser
65                  70                  75                  80
```

Ala Leu Phe Arg Ala Pro Asp Ala Val Asp Arg Val Thr Pro Pro
                85                  90                  95

Ala Glu Pro Leu Asn Arg Met Pro Asp Ala Tyr Arg Ala Tyr Gly Gly
            100                 105                 110

Arg Ala Thr Val Val Asn Asn Tyr Ile Arg Lys Trp Gln Gln Val
            115                 120                 125

Tyr Ser Gln Arg Gly Gly Asn Pro Gln Gln Met Thr Glu Glu Gln Arg
    130                 135                 140

Glu Gln Leu Ser Tyr Gly Cys Val Gly Val Thr Trp Val Asn Thr Gly
145                 150                 155                 160

Pro Tyr Pro Thr Asn Lys Leu Ala Phe Ala Phe Asp Glu Asn Lys
                165                 170                 175

Tyr Lys Asn Asp Leu Glu Asn Ser Arg Pro Arg Pro Asn Glu Thr Gln
                180                 185                 190

Ala Glu Phe Glu Gly Arg Ile Ala Lys Asp Ser Phe Asp Glu Gly Lys
            195                 200                 205

Gly Phe Lys Arg Ala Arg Glu Val Ala Ser Val Met Asn Lys Ala Leu
    210                 215                 220

Asp Asn Ala His Asp Glu Glu Thr Tyr Ile Gly His Leu Lys Thr Glu
225                 230                 235                 240

Leu Ala Asn Lys Asn Asp Ala Leu Leu Tyr Glu Asp Ser Arg Ser Ser
                245                 250                 255

Phe Tyr Ser Ala Leu Arg Asn Thr Pro Ser Phe Lys Glu Arg Asp Gly
                260                 265                 270

Gly Asn Tyr Asp Pro Ser Lys Met Lys Ala Val Val Tyr Ser Lys His
    275                 280                 285

Phe Trp Ser Gly Gln Asp Gln Arg Gly Ser Ser Glu Lys Arg Lys Tyr
    290                 295                 300

Gly Asp Pro Asp Ala Phe Arg Pro Gly Gln Gly Thr Gly Leu Val Asp
305                 310                 315                 320

Met Ser Arg Asp Arg Asn Ile Pro Arg Ser Pro Ala Lys Pro Gly Glu
                325                 330                 335

Ser Trp Val Asn Phe Asp Tyr Gly Trp Phe Gly Ala Gln Ala Glu Ala
                340                 345                 350

Asp Ala Asp Lys Thr Val Trp Thr His Ala Asn His Tyr His Ala Pro
            355                 360                 365

Asn Gly Gly Met Gly Pro Met Asn Val Tyr Glu Ser Lys Phe Arg Asn
    370                 375                 380

Trp Ser Ala Gly Tyr Ala Asp Phe Asp Arg Gly Ala Tyr Val Ile Thr
385                 390                 395                 400

Phe Ile Pro Lys Ser Trp Asn Thr Ala Pro Ala Glu Val Lys Gln Gly
                405                 410                 415

Trp Pro

<210> SEQ ID NO 3
<211> LENGTH: 1257
<212> TYPE: DNA
<213> ORGANISM: Streptomyces platenis

<400> SEQUENCE: 3
atgtacaaac gccggagttt actcgcgttc gccactgtgg gtgcgctgat atgcaccgcc      60
ggagtcatgc cgtcggtcag ccatgccgcc agcggcggcg acggggaatg ggaggggtcc     120
tacgccgaaa cgcacgacct gacggcggag gacgtcaaga acatcaacgc gctgaacaaa     180

-continued

```
agagctctga ctgcgggtca acccgggaat tcgccggcgg aattgtcgcc gagcgccagt       240
gcgctcttcc gggcccccga cgccgtcgat gacagggtga cccctcccgc cgagccgctc       300
aaccggatgc ctgacgcgta ccgggcctac ggaggcaggg ccactacggt cgtcaacaac       360
tacatacgca agtggcagca ggtctacagt caacgcggcg gcaacccaca gcaaatgacc       420
gaagagcagc gagaacaact gtcctacggc tgcgtcggcg tcacctgggt caatacaggc       480
ccctacccga cgaacaaact cgcgttcgcg ttcttcgacg agaacaagta caagaacgac       540
ctggaaaaca gcagaccgcg acccaacgag acgcaggcgg agttcgaggg gcgcatcgcc       600
aaggacagtt tcgatgaggg aaagggtttc aagcgggcgc gtgaggtggc atccgtcatg       660
aacaaggccc tggataacgc gcacgacgag gagacttaca tcggccacct caagacagag       720
ctcgcgaaca aaacgacgc tctgctctac gaggacagcc gctcgagctt ttactcggcg        780
ctgaggaata cgccgtcctt caaggaaagg gatggaggca actacgaccc gtccaagatg       840
aaggcggtgg tctactcgaa gcacttctgg agcgggcagg accagcgggg ctcctccgag       900
aagaggaagt acggtgaccc ggacgccttc cgccccggcc agggcacagg tctggtagac       960
atgtcgaggg acaggaacat tccgcgtagt cccgcaaaac ctggcgaaag ttgggtcaat      1020
ttcgactacg gctggttcgg ggctcaggca gaagcggatg ccgacaaaac cgtatggacc      1080
cacgccaacc actatcatgc gcccaatggc ggcatgggcc ccatgaacgt atacgagagc      1140
aagttccgga actggtctgc ggggtacgcg gacttcgacc gcggagccta cgtcatcacg      1200
ttcataccca agagctggaa caccgccccc gccgaggtga agcagggctg gccgtaa         1257
```